United States Patent
Hsieh

(10) Patent No.: US 8,050,479 B2
(45) Date of Patent: Nov. 1, 2011

(54) METHOD AND SYSTEM FOR GENERATING A COMPUTED TOMOGRAPHY IMAGE

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 485 days.

(21) Appl. No.: 12/393,816

(22) Filed: Feb. 26, 2009

(65) Prior Publication Data
US 2010/0215233 A1    Aug. 26, 2010

(51) Int. Cl.
*G06K 9/00* (2006.01)
*G01N 23/00* (2006.01)

(52) U.S. Cl. ............ 382/131; 378/16; 600/436
(58) Field of Classification Search .......... 382/131; 478/16; 600/436
See application file for complete search history.

(56) References Cited

U.S. PATENT DOCUMENTS

| | | | |
|---|---|---|---|
| 6,816,567 B2 * | 11/2004 | Drummond et al. | 378/16 |
| 2003/0031289 A1 * | 2/2003 | Hsieh | 378/4 |
| 2004/0101086 A1 | 5/2004 | Sabol et al. | |
| 2005/0105679 A1 * | 5/2005 | Wu et al. | 378/22 |
| 2008/0310598 A1 * | 12/2008 | Zhang et al. | 378/207 |
| 2009/0147919 A1 * | 6/2009 | Goto et al. | 378/86 |
| 2010/0128948 A1 * | 5/2010 | Thomsen et al. | 382/131 |
| 2010/0183117 A1 | 7/2010 | Tsumuraya et al. | |

FOREIGN PATENT DOCUMENTS

| EP | 1882449 A1 * | 1/2008 |
|---|---|---|
| WO | 2009011422 A1 | 1/2009 |

OTHER PUBLICATIONS

Search Report & Written Opinion for corresponding NO Application 2004249, Jul. 15, 2010.

* cited by examiner

*Primary Examiner* — Roy M Punnoose

(57) ABSTRACT

A method of generating a computed tomography image is disclosed herein. The method includes acquiring a first plurality of projections at a first energy level and acquiring a second plurality of projections at a second energy level. The method includes reconstructing an image from the first plurality of projections and generating a synthesized projection from the image that corresponds to one of the second plurality of projections. The method includes comparing the synthesized projection to the one of the second plurality of projections and modifying the image to form an updated image based on the comparing the synthesized projection to the one of the second plurality of projections. A computed tomography imaging system is also disclosed.

24 Claims, 2 Drawing Sheets

METHOD AND SYSTEM FOR GENERATING A COMPUTED TOMOGRAPHY IMAGE

FIELD OF THE INVENTION

This disclosure relates generally to the field of medical imaging. In particular, the following techniques relate to multiple-energy computed tomography imaging systems and a method of generating a computed tomography image.

BACKGROUND OF THE INVENTION

Computed tomography (CT) imaging systems operate by projecting an x-ray beam from an x-ray source through an attenuating object, such as a patient. The attenuated x-ray beam is then detected by a detector assembly. Some materials, such as bone, are much more x-ray attenuating than other materials, such as soft tissue. Conventional third-generation CT imaging systems acquire attenuation data by projecting a polychromatic x-ray beam from the x-ray source. The polychromatic x-ray beam contains many different frequencies of x-rays and is typically centered around a particular energy level. With sufficient angular coverage around the patient, cross-sectional images can be formed revealing the inner structure of the scanned object. The images are typically displayed on a flat-screen monitor or cathode ray tube. A virtual 3-D image may also be produced based on data acquired during a computed tomography scan.

However, some materials share very similar x-ray attenuation characteristics at a particular energy level. For example, bone and iodine contrast agent have similar x-ray attenuation characteristics at some commonly used energy levels. As a result, it can be difficult to differentiate materials with similar x-ray attenuation characteristics at a particular energy level. Recently, multiple-energy CT imaging systems have been developed. By collecting x-ray attenuation data at more than one energy level, it is possible to gain additional insight into the nature of the scanned object.

In a conventional third-generation dual-energy CT imaging system, a processor may rapidly switch the output from a generator so that the input voltage to the x-ray source changes from projection to projection. For example, a typical dual-energy CT imaging system may rapidly alternate between acquiring a high-energy projection and a low-energy projection. In order for a conventional dual-energy CT imaging system to work well, the time spent transitioning between the high-energy level and the low-energy level must be short relative to the duration of each projection. Otherwise, the effective energy level during the high-energy projections will be less than the desired high-energy setting and the effective energy level during the low-energy projections will be greater than the desired low-energy setting. Given the fact that the sampling rate for a state-of-the-art third-generation CT imaging system is several kilohertz, the generator must transition between the high-energy level and the low-energy level in significantly less than a fraction of a millisecond. Enabling a generator to switch this quickly places an enormous demand on the generator hardware. Predictably, the demands on hardware will further increase as scan speed increases.

For these and other reasons, there is a need for a multiple-energy CT imaging method and system that significantly reduces the demand on generator hardware without negatively affecting scan time or image quality.

BRIEF DESCRIPTION OF THE INVENTION

The above-mentioned shortcomings, disadvantages and problems are addressed herein which will be understood by reading and understanding the following specification.

In an embodiment, a method of generating a computed tomography image includes acquiring a first plurality of projections at a first energy level and acquiring a second plurality of projections at a second energy level. The method includes reconstructing an image from the first plurality of projections. The method includes generating a synthesized projection from the image that corresponds to one of the second plurality of projections. The method includes comparing the synthesized projection to the one of the second plurality of projections. The method also includes modifying the image to form an updated image based on the comparing the synthesized projection to the one of the second plurality of projections.

In an embodiment, a method of generating a computed tomography image includes acquiring a first plurality of projections at a first energy level. The method includes acquiring a second plurality of projections at a second energy level. The method includes reconstruction an image from the first plurality of projections. The method includes generating a plurality of synthesized projections from the image, each of the plurality of synthesized projections corresponding to one of the second plurality of projections. The method includes comparing each of the plurality of synthesized projections to the corresponding one of the second plurality of projections. The method also includes modifying the image to form an updated image based on the comparing each of the plurality of synthesized projections to the corresponding one of the second plurality of projections.

In an embodiment, a method of generating a computed tomography image includes acquiring a first plurality of projections of an object at a first energy level. The method includes acquiring a second plurality of projections of the object at a second energy level. The method includes reconstructing an image of the object at the first energy level from the first plurality of projections. The method also includes modifying the image to generate an updated image of the object, wherein the updated image represents the object at the second energy level.

In an embodiment, a computed tomography imaging system includes a gantry, an x-ray source attached to the gantry, a table adapted to translate with respect to the gantry, and a processor in electrical communication with the gantry, the x-ray source, and the table. The processor is configured to acquire a first plurality of projections at a first energy level and to acquire a second plurality of projections at a second energy level. The processor is configured to reconstruct an image from the first plurality of projections. The processor is configured to generate a synthesized projection from the image that corresponds to one of the second plurality of projections. The processor is configured to determine a difference between the synthesized projection and the one of the second plurality of projections. The processor is also configured to generate an updated image by modifying the first image based on the difference between the synthesized projection and the one of the second plurality of projections.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
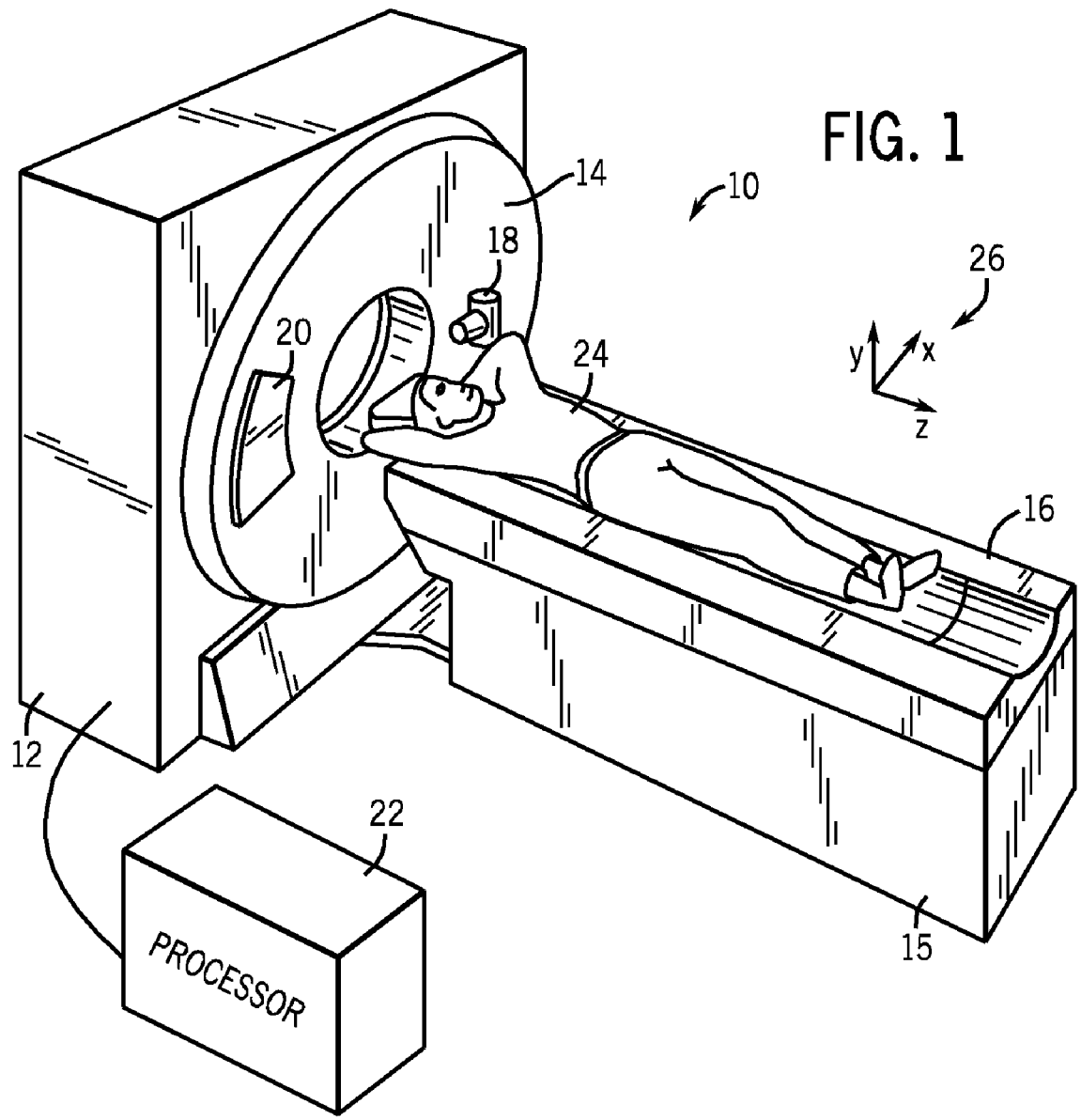
FIG. 1 is a schematic representation of a computed tomography imaging system in accordance with an embodiment.

Referring to FIG. 1, a schematic representation of a computed tomography (CT) imaging system 10 according to an embodiment is shown. The CT imaging system 10 includes a gantry support 12, a gantry 14, a table support 15, a table 16, an x-ray generator (not shown), an x-ray source 18, a detector assembly 20, and a processor 22. The gantry 14 is configured to rotate within the gantry support 12. The gantry 14 is adapted to retain the x-ray source 18 and the detector assembly 20. The x-ray generator is configured to deliver both a high-voltage input and a low-voltage input to the x-ray source 18. According to an embodiment, the high-voltage input may comprise a 140 kVp input while the low-voltage input may comprise an 80 kVp input. The x-ray source 18 receives either the high-voltage input or the low-voltage input from the generator and emits an x-ray beam. If the x-ray source 18 receives the high-voltage input, the x-ray beam will comprise a high-energy x-ray beam. If the x-ray source 18 receives the low-voltage input, the x-ray beam will comprise a low-energy x-ray beam. Both the high-energy x-ray beam and the low-energy x-ray beam comprise photons from a wide energy spectrum. One skilled in the art should appreciated that the term "high-energy x-ray beam" indicates that the highest energy x-ray photons in the high-energy x-ray beam are of high energy and that the term "low-energy x-ray beam" indicates that the highest energy x-ray photons in the low-energy x-ray beam are of low energy. Also, for the purposes of this disclosure, the terms "high-energy x-ray beam" and "low-energy x-ray beam" are relative to each other, and they should not be interpreted as indicating an absolute level of energy.

The x-ray source 18 is configured to emit either a high-energy x-ray beam or a low-energy x-ray beam through a patient 24 being examined. After passing through the patient 24, either the high-energy x-ray beam or the low-energy x-ray beam is received at the detector assembly 20. The detector assembly 20 comprises a plurality of detector elements (not shown). Each of the plurality of detector elements produces an electrical signal that varies based on the intensity of the x-ray beam received during a sampling interval. The table 16 is adapted to translate the patient 24 in a z-direction with respect to the gantry 14 as indicated by a coordinate axis 26. The processor 22 is configured to control the rotation of the gantry 14, the position of the table 16, and the activation of the x-ray source 18.

Figure 2:
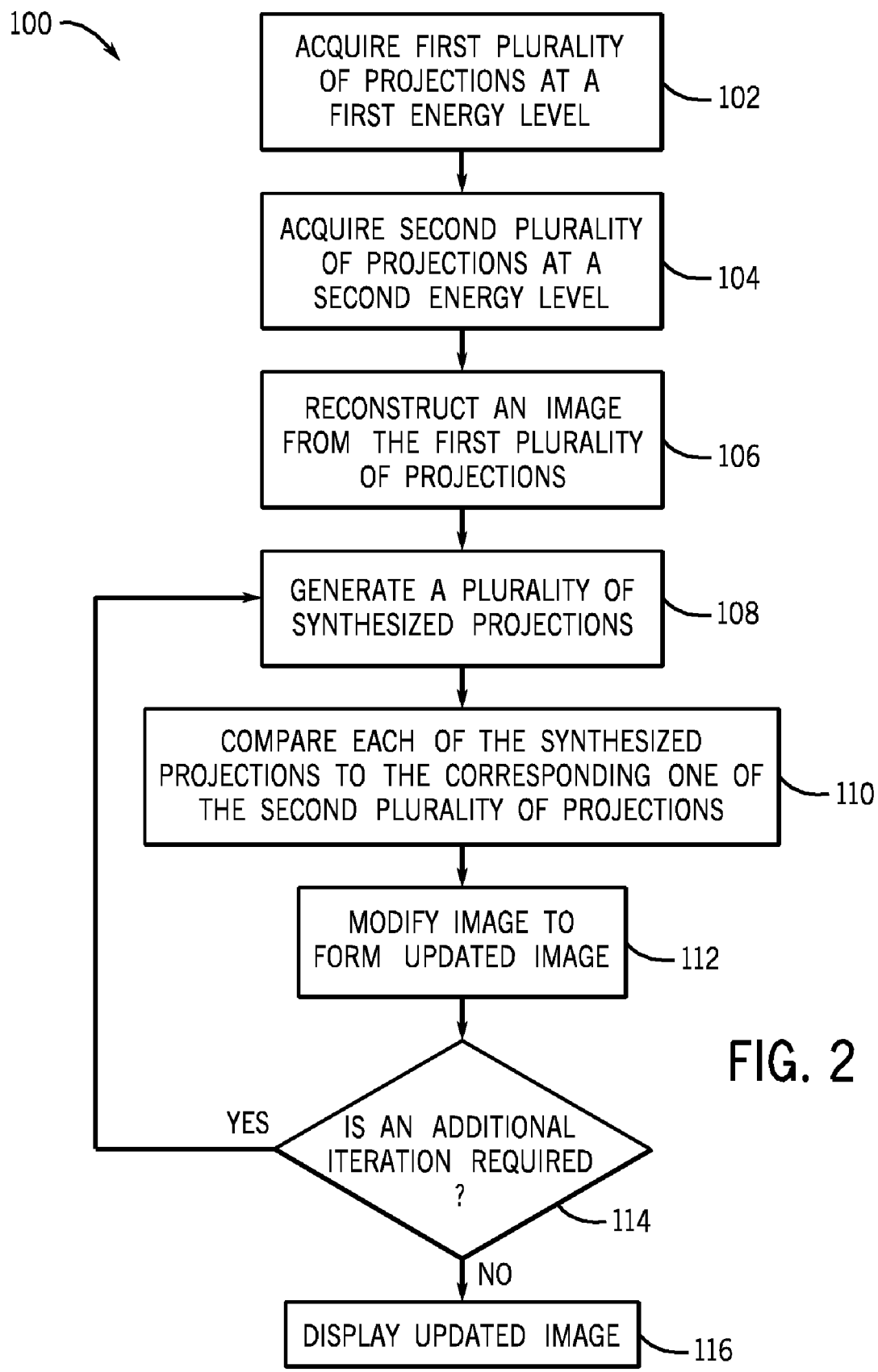
FIG. 2 is a flow chart illustrating a method of generating a computed tomography image in accordance with an embodiment.

Having described the structure of the CT imaging system 10, a method 100 will be described hereinafter. FIG. 2 is a flow chart representing the method 100 in accordance with an embodiment. The individual blocks 102-116 represent steps that may be performed in accordance with the method 100. The steps 102-116 of the method 100 need not be performed in the order shown. The technical effect of the method 100 is the generation of computed tomography image.

Referring to both FIG. 1 and FIG. 2, the processor 22 may be configured to implement the steps illustrated in the method 100. At step 102, the processor 22 controls the generator (not shown) in a manner so that the x-ray source 18 emits an x-ray beam at a first energy level. According to an embodiment, the first energy level may be a relatively high energy level, such as 140 kVp. The processor 22 controls the generator, the x-ray source 18, the gantry 14, and the table 16 so that a first plurality of projections are acquired at the first energy level. The first plurality of projections may be acquired as part of a helical acquisition according to an embodiment and as part of an axial acquisition according to another embodiment.

For third-generation CT systems, a projection may be defined to include data obtained at generally the same time from some or all of the detector elements for a given gantry angle and location along the z-axis. In a third-generation CT imaging system a projection may comprise the output from all of the detector elements at generally the same time. The number of projections that can be acquired depends upon the speed of gantry rotation, the type of hardware used in the detector assembly 20, and the number of detector elements among other factors. According to an embodiment, 984 projections may comprise a complete set of projections for one gantry revolution.

At step 104, the processor 22 controls the generator (not shown) in a manner so that the x-ray source 18 emits an x-ray beam at a second energy level. According to an embodiment, the second energy level may be a relatively low energy level, such as 80 kVp. The processor 22 controls the generator, the x-ray source 18, the gantry 14, and the table 16 so that a second plurality of projections are obtained at the second energy level. The second plurality of projections may be acquired as part of a helical acquisition according to an embodiment or as part of an axial acquisition according to another embodiment. Steps 102 and 104 may be performed simultaneously, sequentially, or a combination of simultaneously and sequentially. According to an embodiment where steps 102 and 104 are performed simultaneously, the first plurality of projections are acquired during generally the same period of time that the second plurality of projections are acquired. For example, the method 100 may alternate between acquiring one or more projections at the first energy level and acquiring one or more projections at the second energy level. According to this example, the first plurality of projections would comprise all of the projections acquired at the first energy level and the second plurality of projection would comprise all of the projections acquired at the second energy level.

It is well-known by those skilled in the art that an image produced by an x-ray beam at a higher energy level may generally produce less noise than an image produced by an x-ray beam at a lower energy level if all other imaging parameters are held constant. Therefore, according to an embodiment, it may be preferable to collect more projections at the higher energy level than at the lower energy level. According to an embodiment, the processor 22 may control the generator (not shown) and x-ray source 18 in a manner so that one lower energy projection is acquired for every 24 projections. According to an exemplary embodiment, projections 1 through 23 may be acquired at a first energy level, such as 140 kVp, and projection 24 may be acquired at a second energy level, such as 80 kVp. All 984 projections of the exemplary embodiment may be acquired by alternating between acquiring 23 projections at 140 kVp and acquiring one projection at 80 kVp. Therefore, according to the exemplary embodiment, the result will be 943 projections at 140 kVp and 41 projections at 80 kVp. It should be understood that other embodiments may collect the first plurality of projections and the second plurality of projection in an entirely different manner.

In accordance with the previously described exemplary embodiment, the first plurality of projections comprises 943 projection acquired at 140 kVp and the second plurality of projections comprises 41 projections acquired at 80 kVp. Several or all of the 41 projections acquired at 80 kVp may be separated by a common angle. For example, according to an embodiment, there may be a common angle of approximately 8.8 degrees separating each of the 41 projections acquired at 80 kVp. According to another embodiment, some or all of the 41 projections acquired at 80 kVp may be separated by an amount that varies. For example, some of the projections may be spaced apart by 2 degrees or less and others of the projections may be spaced apart by more than 10 degrees. The amount of angular separation between projections at a particular energy level may be determined by many factors including hardware limitations of the CT imaging system 10 (shown in FIG. 1).

According to an embodiment, a half-scan may be used during the acquisition of the first plurality of projections and the second plurality of projections to improve the temporal resolution of the CT imaging system. Half-scans are well-known by those skilled in the art. In accordance with an embodiment using a half-scan, a total of 616 projections are acquired at 140 kVp and 27 projections are acquired at 80 kVp. Other embodiments may acquire a different ratio of projections acquired at a first energy level to projections acquired at a second energy level.

In accordance with other embodiments, projections may be acquired at three or more different energy levels. For example, according to an embodiment, a first plurality of projections may comprise 902 projections at 140 kVp, a second plurality of projections may comprise 41 projections at 100 kVp, and a third plurality of projections may comprise 41 projections at 80 kVp. According to an embodiment, the first plurality of projections, the second plurality of projections, and the third plurality of projections may be acquired in an interleaved manner. In other words, the processor 22 (shown in FIG. 1) may rotate between acquiring one or more projections at each of the three energy levels.

In accordance with another embodiment, the generator (not shown) may utilize a slower transition when switching between energy levels. According to one embodiment, 943 projections are acquired at 140 kVp and 41 projections are acquired at 80 kVp. Each of the 41 projections acquired at 80 kVp may be evenly spaced apart. The projections that are immediately before or after each of the projections acquired at 80 kVp projection may be collected while the generator is in a transition zone. For the purposes of this disclosure, the term "transition zone" includes a time when the generator is between two of the desired voltages. In accordance with an exemplary embodiment, the spectrum of the x-ray beam may be somewhere between the desired levels of 80 kVp and 140 kVp during each of the transition zones. The demand on the generator is significantly reduced by acquiring projections during the transition zones instead of requiring that the generator is at exactly 140 kVp immediately before and after each 80 kVp projection.

According to another embodiment, the x-ray tube current used when acquiring the projections at the first energy level may be substantially different than the x-ray tube current used when acquiring the projections at the second energy level. For example, according to an embodiment designed to reduce x-ray dose, the processor 22 may utilize a reduced x-ray tube current level while acquiring the projections at the higher energy level. The reduced x-ray tube current level is reduced in comparison to the x-ray tube current level used while acquiring the projections at the lower energy level. According to another embodiment, the duration of a projection acquired at first energy level may be significantly different than the duration of a view acquired at second energy level.

Still referring to FIG. 2, at step 106 an image is reconstructed from the first plurality of projections. According to the previously described exemplary embodiment, the image is reconstructed from the 943 projections acquired at 140 kVp. Since 943 projections at 140 kVp represents an almost complete set of projections, the first image may be reconstructed by using a conventional reconstruction algorithm, such as a filtered back-projection algorithm. If a filtered back-projection algorithm is used to reconstruct the first image, it may be necessary to estimate any missing projections. For the purposes of this disclosure, the term "image" includes a reconstructed volume from one or more slices of computed tomography data. For example, for a multi-slice CT imaging system, an image may comprise data from a plurality of slices. According to the previously described exemplary embodiment, 943 projections were acquired 140 kVp and 41 of the projections were acquired at 80 kVp. This embodiment is missing 41 projections from the 140 kVp set of projections. The missing projections may be estimated by performing a linear interpolation or a high-order interpolation based on adjacent projections that were acquired at 140 kVp. It should be appreciated that the first image may be reconstructed through other techniques according to additional embodiments. For example, an iterative reconstruction technique may be used to generate the first image.

At step 108, a plurality of synthesized projections are generated. According to an embodiment, the plurality of synthesized projections are based on the image the first time the method 100 reaches step 108. According to an embodiment with multiple iterations, a plurality of synthesized projections may be generated based on the updated image in subsequent iterations as will be described hereinafter. For purposes of this disclosure, the term "synthesized projection" is defined to include a forward projection from an image. Normally, a CT imaging system collects a plurality of projections and uses the projections to reconstruct an image. However, in the case of a synthesized projection, an image is used as the input and the synthesized projection represents what the projection would most likely comprise at a particular location and gantry angle. Synthesized projections are well-known by those skilled in the art. Each of the synthesized projections generated at step 108 may correspond to one of the second plurality of projections. For the purposes of this disclosure, a projection and a synthesized projection are considered to correspond if they both represent generally the same location and gantry angle of the same object. Additional normalization steps may be used to adjust the scale of the synthesized projection. For example, according to another embodiment, one of the plurality of synthesized projections generated at step 108 may represent the same location and gantry angle as one of the first plurality of projections acquired at step 102. Then, a scaling factor or a plurality of polynomial parameters may be determined based on a comparison of the synthesized projection and the corresponding one of the first plurality of projections. The scaling factor or the plurality of polynomial parameters may be used to adjust each of the synthesized projections generated at step 108.

According to an embodiment, each of the plurality of synthesized projections generated at step 108 corresponds to one of the second plurality of projections. Therefore, each one of the synthesized projections is generated at the same gantry angle and location in the z-direction as one of the second plurality of projections. According to the previously described exemplary embodiment, the second plurality of projections comprises 41 projections that were acquired at 80 kVp. Each of the plurality of synthesized projections corresponds to one of the 41 projections that were acquired at 80 kVp. In other words, the plurality of synthesized projections represent the same locations and angles as the 41 projections that were acquired at 80 kVp during step 104. It is not necessary for the plurality of synthesized projections and the second plurality of projections to be of the same number in all embodiments.

According to another embodiment, there may be only four synthesized projections generated during step 108. The four synthesized projections may be separated by approximately 45 degrees from each other. It should be appreciated that each of the four synthesized projections still corresponds to one of the second plurality of projections acquired during step 104. According to an additional embodiment, step 108 may be replaced with a step where only one synthetic projection is generated for each iteration.

At step 110, each of the plurality of synthesized projections is compared to the corresponding one of the second plurality of projections. A difference and/or a ratio may be calculated between each synthesized projection and the corresponding one of the second plurality of projections. For example, if the synthesized projections were generated from an image acquired at 140 kVp and the second plurality of projections were acquired at 80 kVp, any difference between a synthesized projection and the corresponding one of the second plurality of projections may be assumed to be from the mean energy difference between the x-ray beam produced at 140 kVp and the x-ray beam produced at 80 kVp.

At step 112, the first image is modified based on the comparison performed at step 110 to form an updated image. According to an embodiment, a difference between each of the synthesized projections generated at step 108 and the corresponding projection acquired as part of the second plurality of projections during step 104 is distributed according to the following equation:

$$\Delta f(x,y,z) = \xi[f(x,y,z)] \times \eta[\Delta p(\gamma,\beta,\alpha)]$$

where f(x, y, z) is a CT number of a voxel in an image, Δf(x, y, z) is an update value for this voxel, ξ is a function, and η is a function. According to an embodiment, ξ may be a monotonically increasing function. In another embodiment, ξ may be a piecewise continuous function. The function ξ is based on CT number due to the observation that almost all CT imaging systems are calibrated based on water. That is, if the scanned object is made of water only, the reconstructed image will have a mean CT number of zero Hounsfield Units (HU) regardless of the energy level. In other words, an image of an object made only of water will be the same if acquired at an energy level of 80 kVp or if it was acquired at an energy level of 140 kVp. Therefore, for the portion of the image with CT numbers close to zero, there is very little need for adjustment between the 140 kVp and 80 kVp energy levels. Instead, the adjustment is needed mainly for the material in the scanned object that is significantly different from water. Δp(γ, β, α) is the difference between one of the plurality of synthesized projections and the corresponding one of the second plurality of projections. According to an embodiment, γ, β, and α are respectively the fan-angle, projection angle, and cone angle corresponding to the image voxel (x, y, z). The function η is a mapping function used to adjust the intensity of the updated image based on a path-length at the projection sample (γ, β, α).

For example, for a fixed projection difference, the function η may result in a smaller amount of adjustment per voxel for a long path-length through the object than for a shorter path-length through the object since the difference needs to be distributed over a larger number of voxels.

According to an embodiment, the following update function may be used to form an updated image at step 112:

$$\Delta f(x,y,z) = \left[\frac{\langle f(x,y,z)-t, 0\rangle}{m}\right] \frac{p(\gamma,\beta,\alpha) - p'(\gamma,\beta,\alpha)}{\langle p'(\gamma,\beta,\alpha), s\rangle}$$

where ⟨f(x, y, z)−t,0⟩ is a function that forces f(x, y, z) to be larger or equal to t,0; f(x, y, z) is a CT number of a voxel in an image; p(γ, β, α) is a projection acquired during step 104 passing through voxel (x, y, z); p'(γ, β, α) is a corresponding synthesized projection; ⟨p'(γ, β, α), s⟩ forces p'(γ, β, α) to be equal or larger than s; and t, m, and s are parameters.

One of the goals of the update function may be to generate an image of a patient or an object at the second energy level even though only an incomplete set of projections were acquired at the second energy level. For example, an image may be reconstructed from a first plurality of projections acquired at 140 kVp and it is desired to generate an image at 80 kVp. According to another embodiment, it may be possible to realize a reduction in x-ray dose by initially reconstructing an image at first energy level and then using the update function to generate an image at a second energy level that is higher than the first energy level.

Still referring to step 112, according to an embodiment, modifying the image comprises applying an update function to the image that varies based on a CT number of a voxel in the image. As was described previously, experimental results have shown that there is a relatively small difference between the soft-tissue or water portion of an image at 80 kVp and the soft-tissue or water portion of an image at 140 kVp. Conversely, it is known that there is a relatively large difference between bone at 80 kVp and bone at 140 kVp. Therefore, if the first image, reconstructed from data acquired at 140 kVp, is used as an initial assumption, it should not be necessary to significantly change the voxel values in regions with CT numbers close to that of water when modifying the 140 kVp image to form an image at 80 kVp. On the other hand, there should be more significant changes to areas with relatively high CT numbers in the image. According to an embodiment, the update function may be weighted so that voxels with relatively high CT numbers, such as bone and iodine, are modified more than voxels with relatively low CT numbers, such as soft tissue. By making the update function dependent on the CT number of the voxels in the image, it is possible for the method 100 to converge on the desired image, such as the 80 kVp image, more quickly. Additionally, by using an update function that only makes small changes to portions of the image with CT numbers close to that of water, streaking artifacts caused by dense objects may be significantly reduced or eliminated. While the energy levels of 80 kVp and 140 kVp have been used as exemplary energy levels in this disclosure, it should be appreciated by those skilled in the art that additional embodiments my use energy levels significantly different than 80 kVp and/or 140 kVp.

At step 114, the processor 22 (shown in FIG. 1) determines if an additional iteration is required. According to an embodiment, the processor 22 determines if the difference between each of the plurality of synthesized projections and the corresponding one of the second plurality of projections is within an acceptable limit. According to another embodiment, the processor 22 determines if the method 100 has looped through steps 108-114 a predetermined number of times. Other embodiments may use additional methods of determining if additional iterations are required at step 114. If an additional iteration is required at step 114, the method 100 returns to step 108 where a plurality of synthesized projections are generated from the updated image of step 112. Iteratively modifying the image by looping through steps 108-114 from three to five times has produced favorable results according to experimental data.

If no additional iterations are necessary at step 114, the method 100 proceeds to step 116, where the updated image is displayed. According to other embodiments, step 116 may be replaced by a step where the image is stored instead of being displayed. The stored image may then be used in a subsequent step. According to an embodiment, the updated image represents an image at the second energy level. It should be noted that by using the method 100, it may be possible to generate an image of acceptable image quality at the second energy level even though too few projections were acquired at step 104 for an image to be reconstructed using a conventional reconstruction algorithm.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A method of generating a computed tomography image comprising:
    acquiring a first plurality of projections at a first energy level;
    acquiring a second plurality of projections at a second energy level;
    reconstructing an image from the first plurality of projections;
    generating a synthesized projection from the image that corresponds to one of the second plurality of projections;
    comparing the synthesized projection to said one of the second plurality of projections; and
    modifying the image to form an updated image based on said comparing the synthesized projection to said one of the second plurality of projections.

2. The method of claim 1, wherein the first energy level comprises a higher energy level than the second energy level.

3. The method of claim 1, wherein the first energy level comprises a lower energy level than the second energy level.

4. The method of claim 1, wherein said comparing the synthesized projection to said one of the second plurality of projections comprises calculating a difference between the synthesized projection and said one of the second plurality of projections.

5. The method of claim 1, wherein said modifying the image comprises applying an update function that varies based on a CT number.

6. The method of claim 1, further comprising displaying the updated image.

7. The method of claim 1, wherein the updated image represents the second energy level.

8. The method of claim 1, wherein the first plurality of projections contains more than 5 times the number of projections as the second plurality of projections.

9. The method of claim 1, wherein the second plurality of projections comprises two or more projections separated by a common angle.

10. The method of claim 1, wherein the second plurality of projections comprises 4 projections separated by 45 degrees.

11. A method of generating a computed tomography image comprising:
    acquiring a first plurality of projections at a first energy level;
    acquiring a second plurality of projections at a second energy level;
    reconstructing an image from the first plurality of projections;
    generating a plurality of synthesized projections from the image, each of the plurality of synthesized projections corresponding to one of the second plurality of projections;
    comparing each of the plurality of synthesized projections to the corresponding one of the second plurality of projections; and
    modifying the image to form an updated image based on said comparing each of the plurality of synthesized projections to the corresponding one of the second plurality of projections.

12. The method of claim 11, wherein said modifying the image comprises applying an update function that varies based on a CT number.

13. The method of claim 11, wherein said comparing comprises calculating a difference between each of the plurality of synthesized projections and the corresponding one of the second plurality of projections.

14. A method of generating a computed tomography image comprising:
    acquiring a first plurality of projections of an object at a first energy level;
    acquiring a second plurality of projections of the object at a second energy level;
    reconstructing an image of the object at the first energy level from the first plurality of projections;
    modifying the image to generate an updated image of the object, wherein the updated image represents the object at the second energy level.

15. The method of claim 14, wherein said modifying the image comprises iteratively modifying the image.

16. The method of claim 14, wherein iteratively modifying the image comprises four or more iterations.

17. The method of claim 14, further comprising acquiring a third plurality of projections at a third energy level.

18. The method of claim 17, further comprising modifying the image to generate a second updated image, wherein the second updated image represents the third energy level.

19. A computed tomography imaging system comprising;
    a gantry;
    an x-ray source attached to the gantry;
    a table adapted to translate with respect to the gantry; and
    a processor in electrical communication with the gantry, the x-ray source, and the table, wherein the processor is configured to:
        acquire a first plurality of projections at a first energy level;
        acquire a second plurality of projections at a second energy level;
        reconstruct an image from the first plurality of projections;

generate a synthesized projection from the image that corresponds to one of the second plurality of projections;

determine a difference between the synthesized projection and said one of the second plurality of projections; and generate an updated image by modifying the first image based on the difference between the synthesized projection and said one of the second plurality of projections.

20. The computed tomography imaging system of claim 19, wherein the processor is further configured to display the updated image.

21. The computed tomography imaging system of claim 19, wherein the first energy level exceeds the second energy level.

22. The computed tomography imaging system of claim 19, wherein the second energy level exceeds the first energy level.

23. The computed tomography imaging system of claim 19, wherein the updated image represents the second energy level.

24. The computed tomography imaging system of claim 19, wherein the processor is further configured to apply an update function that varies based on a CT number of a voxel in the image.

* * * * *